United States Patent [19]

Kaczynski et al.

[11] Patent Number: 4,754,401
[45] Date of Patent: Jun. 28, 1988

[54] SYSTEM FOR SERVICING A REMOVABLE RAM PACKAGE FOR AN AMBULATORY MEDICAL MONITOR

[75] Inventors: Francis X. Kaczynski, Bothell; Luke A. F. Merry, Seattle, both of Wash.

[73] Assignee: SpaceLabs, Inc., Bothell, Wash.

[21] Appl. No.: 859,538

[22] Filed: May 5, 1986

[51] Int. Cl.⁴ .............................................. G06F 15/21
[52] U.S. Cl. ...................................... 364/413; 365/63
[58] Field of Search ............... 364/483, 413, 415, 900, 364/200; 365/195, 63, 226; 371/21

[56] References Cited

U.S. PATENT DOCUMENTS

| | | | |
|---|---|---|---|
| 4,236,217 | 11/1980 | Kennedy | 364/900 |
| 4,258,430 | 3/1981 | Tyburski | 364/900 |
| 4,361,877 | 11/1982 | Dyer | 364/900 |
| 4,400,783 | 8/1983 | Locke | 364/900 |
| 4,417,306 | 11/1983 | Citron | 364/415 |
| 4,420,819 | 12/1983 | Price | 364/900 |
| 4,592,018 | 5/1986 | Wiegman | 365/195 |
| 4,618,929 | 10/1986 | Miller | 364/415 |

Primary Examiner—Michael R. Fleming
Attorney, Agent, or Firm—Seed and Berry

[57] ABSTRACT

An apparatus for servicing a removable RAM package of an ambulatory medical monitor is disclosed. The RAM package comprises a RAM for storing blood pressure data and operating parameters and a real time timer. Both are coupled to a multipin edge connector by parallel multibit data and address buses. An adapter for servicing the RAM package by a scanner controller through a standard serial interface is provided. The adapter comprises a microcomputer chip coupled between an RS-232 serial interface and a multipin edge connector for mating engagement with the edge connector on the RAM package. Servicing includes writing and reading data from the RAM package, and reading and setting the time in the real time timer. The apparatus further includes means for controlling access to the adapter by the scanner controller using an identification and unlocking scheme. The system will not unlock if a RAM package is not coupled to the adapter.

15 Claims, 6 Drawing Sheets

SYSTEM FOR SERVICING A REMOVABLE RAM PACKAGE FOR AN AMBULATORY MEDICAL MONITOR

BACKGROUND OF THE INVENTION

The present invention relates to an interface apparatus for a removable RAM package for a data acquisition system, such as an ambulatory blood pressure monitoring system. In particular, the present invention has utility for servicing the RAM package through a standard serial communications link.

A number of portable monitoring devices are used in medical monitoring. One well known device is the so-called Holter monitor which is an EKG monitor which typically uses a magnetic tape recorder to record EKG signals from a patient over extended periods of time. Another is a portable monitor for obtaining blood pressure readings over extended periods of time, such as the Model 5200 ambulatory blood pressure monitor sold by Space-Labs, Inc. of Redmond, WA.

The Model 5200 comprises a blood pressure cuff (described in U.S. Pat. No. 4,206,765), an air pump for activating the blood pressure cuff and a removable RAM package for storing the blood pressure data and timing parameters for controlling automatically when the blood pressure readings are to be taken. The RAM package is described in co-pending U.S. patent application Ser. No. 527,453, filed Aug. 29, 1983, now U.S. Pat. No. 4,592,018 entitled "Removable RAM Package For Ambulatory Medical Monitor". It comprises a RAM and real time timer circuit. The RAM package is detachable from the portable monitor and is inserted into a portable operating system or special adapter for a PC for unloading the blood pressure data.

The RAM has a plurality of data lines and address lines coupled in parallel to an edge connector. The real time timer also has a plurality of data lines coupled to the data lines of the RAM on a common data bus, and address lines coupled to the edge connector. The addressing and data storage and retrieval is done in parallel.

Currently the RAM package is serviced through a unique hardware interface to a personal computer. In order to service the RAM package, a suitable computer with equally suitable interface hardware must be on hand.

The present invention provides means whereby the RAM package can be accessed and serviced through a standard serial interface. A compatible computer need not be on hand, since the servicing can be accomplished remotely through the telephone network using a modem. Thus, the support requirements for servicing a RAM package on site are reduced from a compatible computer with unique interface hardware to an inexpensive interface and an off the shelf modem.

SUMMARY OF THE INVENTION

The present invention provides for an apparatus for servicing a removable RAM package of an ambulatory monitor from a remote scanner controller, a removable RAM package and an intermediate means for adapting the RAM package for servicing by the scanner controller through a standard serial interface. The invention further provides for a system for servicing the removable RAM package which includes the above apparatus in combination with a scanner controller.

The RAM package includes a RAM and a real time timer coupled to an edge connector via parallel multibit data and address buses. The adapting means includes a serial interface connector, such as an RS-232 interface, for coupling to the scanner controller either directly or though a telephone modem. The adapting means further comprises a microcomputer chip responsive to commands from the scanner controller for servicing the RAM package. The microcomputer chip is coupled via parallel multibit address and data buses to an edge connector adapted for mating engagement with the edge connector of the RAM package. The adapting means further comprises a programmable memory chip coupled to the microcomputer chip via the address and data buses.

The adapting means of the system is capable of reading the blood pressure data, control data and timing information stored in the RAM or real time timer to the scanner controller through the serial interface in response to commands from the scanner controller. Similarly, information can be written to the RAM and real time timer.

The system further includes means for controlling access to the adapting means including means for identifying the adapting means and means in response to the identifying means for unlocking the adapting means to allow data communication between the scanner controller and the RAM package.

The access control means further comprises means for preventing the unlocking of the serial interface in response to the absence of a RAM package. The RAM package includes an interlock circuit which provides a READY signal to the prevention means when a RAM package is coupled to the adapting means.

DETAILED DESCRIPTION OF THE DRAWINGS

Figure 1A:
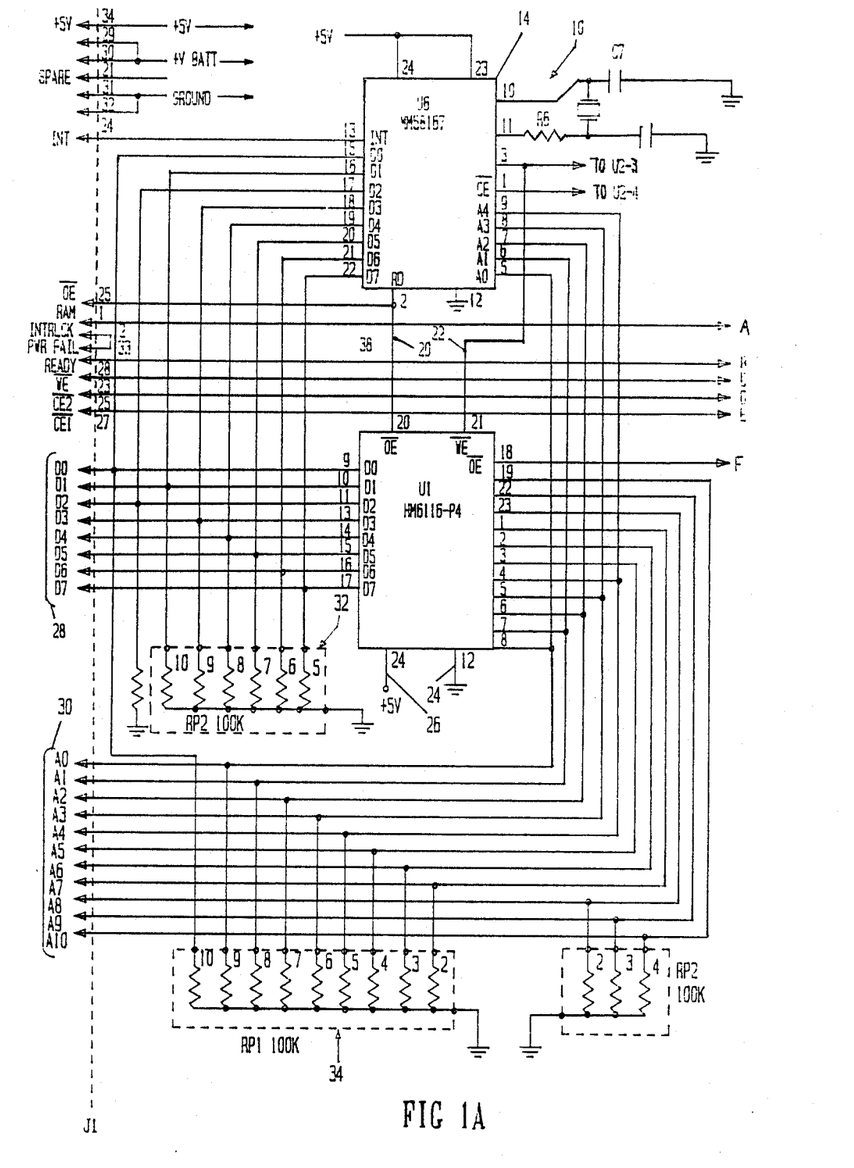
FIGS. 1A and 1B illustrate the circuitry of the removable RAM package used with the present invention.
Figure 1B:
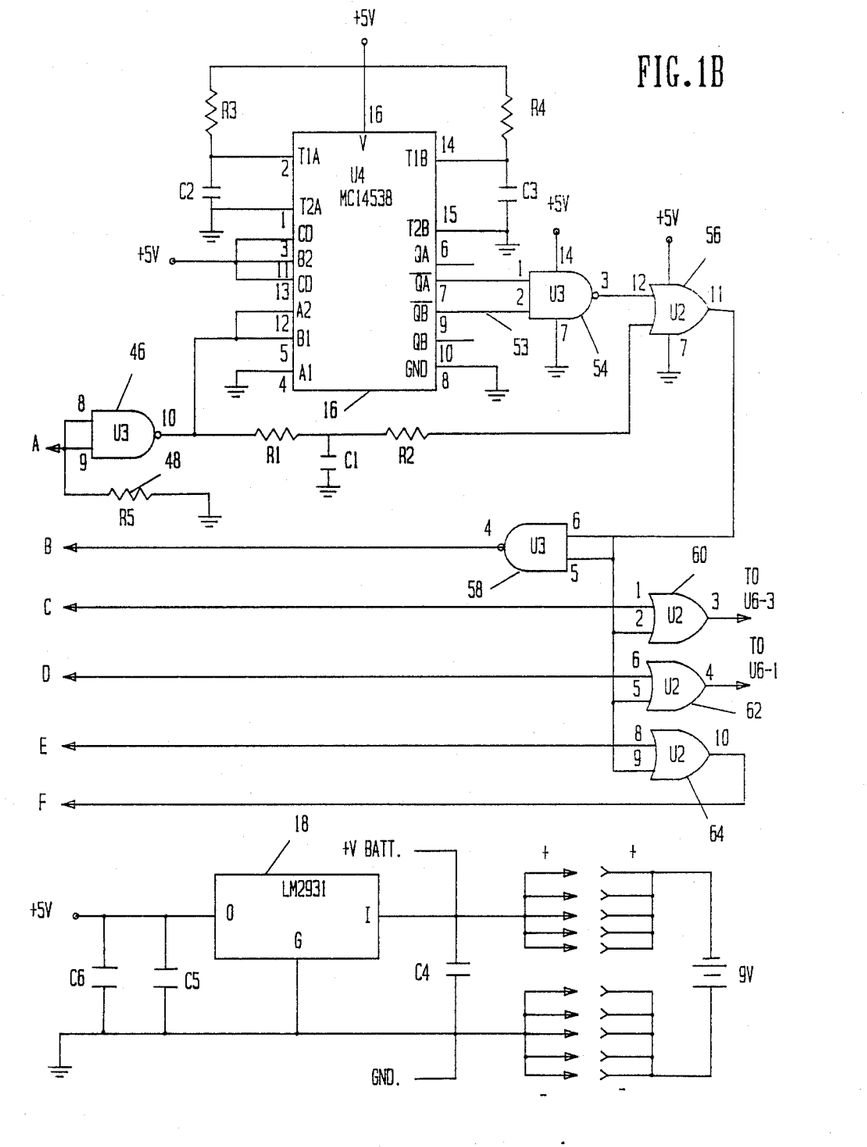

Referring generally to FIG. 1, a removable RAM package 10 is comprised of RAM 12, a real time timer circuit 14, a dual one shot monostable multivibrator 16, and a voltage regulator 18. In the preferred embodiment, the RAM 12 is a 2K×8 CMOS static RAM such as an HM6116, and the real time timer circuit 14 is a National Semiconductor MM58167 Microprocessor Compatible Real Time Clock Circuit.

The RAM 12 has a series of data lines D0–D7 and address lines A0–A10, an output enable line 20, a write enable line 22, and ground and positive power supply connections 24, 26, respectively. The real time timer 14 also has a series of data lines D0–D7, which are connected to the data lines D0-D7 of the RAM 12 on a common data bus 28. The real time timer circuit 14 is also connected to address lines A0-A4 on an address bus 30 which is also connected to the RAM 12. Each of the lines of the data bus 28 and each of the lines of the address bus 30 are connected to ground via a series of 100K resistors 32, 34, respectively.

Figure 2:
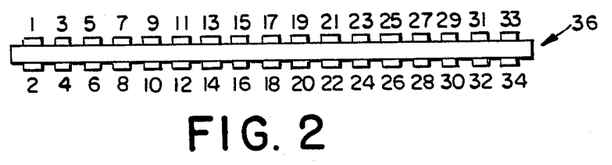
FIG. 2 illustrates the edge connector of the removable RAM package used with the present invention.

Referring now to FIG. 2, an end view of the edge connector 36 which is used to connect the removable RAM package 10 to an external device is shown. The contacts on the edge connector 36 are numbered from 1 through 34, as shown, with the odd numbered contacts being on the top of the edge connector 36 and the even numbered contacts being on the bottom of the edge connector 36.

With reference again to FIG. 1, the number 1 pin of edge connector 36 (see line 38 coupled thereto) provides the input to an inverter circuit 46. Normally, the input to inverter circuit 46, is kept low by a 10K pull-down resistor 48 when the removable RAM package 10 is not connected to an external device. When the removable RAM package 10 is properly connected to an external device, such as the adapter of FIG. 3 to be described in more detail hereinafter, the voltage level on line 38 will be taken high and the output of the inverter 46 forced low. The negative going signal at the input of the dual one shot 16, a Motorola MC14538 integrated circuit in the preferred embodiment of the invention, causes line 52 to NAND gate 54 to go low for approximately 1.25 seconds (based upon the values of R3, R4, C2, and C3). That causes the output of NAND gate 54 to go high for approximately 1.25 seconds, causing the output of OR gate 56 to go high. The high output on OR gate 56 brings the output of NAND gate 58, corresponding to the READY signal on line 28 of edge connector 36, low.

The high output signal from OR gate 56 also causes the outputs of OR gates 60, 62, and 64 to go high. High outputs from gates 60, 62, and 64 disable the RAM and timer chips 12, 14. Both the RAM and timer chips 12, 14 remain disabled until there are no more transitions on the line 38 for more than 1.25 seconds. Any additional upward transitions on the line 38 line will keep the RAM and timer chips 12, 14 disabled for the reasons set forth above. Similarly, any additional downward transitions on the line 38 will keep the RAM and timer chips 12, 14 disabled for 1.25 seconds, as the input line 53 to NAND gate 54 will be forced low. Accordingly, the signal on the line 38 must be stable in a high state for more than 1.25 seconds to allow the one shot 16 to stop timing out and to cause its pin 7 to go high thereby causing the output of NAND gate 54 and OR gate 56 to go low and stay low. This also causes the output of NAND gate 58 to go high, i.e. placing a high signal on the READY line, indicating to the external device that the removable RAM package 10 is ready for data acquisition. The same signal also allows writes to the RAM and timer chips 12, 14 since the outputs of OR gates 60, 62, and 64 will be controlled by the Write Enable and Chip Enable signals on edge connector 36 pins 23, 26, and 27, respectively, since the line 38 controlled inputs of OR gates 60, 62, and 64 will be low, so the outputs of OR gates 60, 62, and 64 will be controlled exclusively by the inputs from the external device on pins 23, 26, 27 of the edge connector 36.

Figure 3:
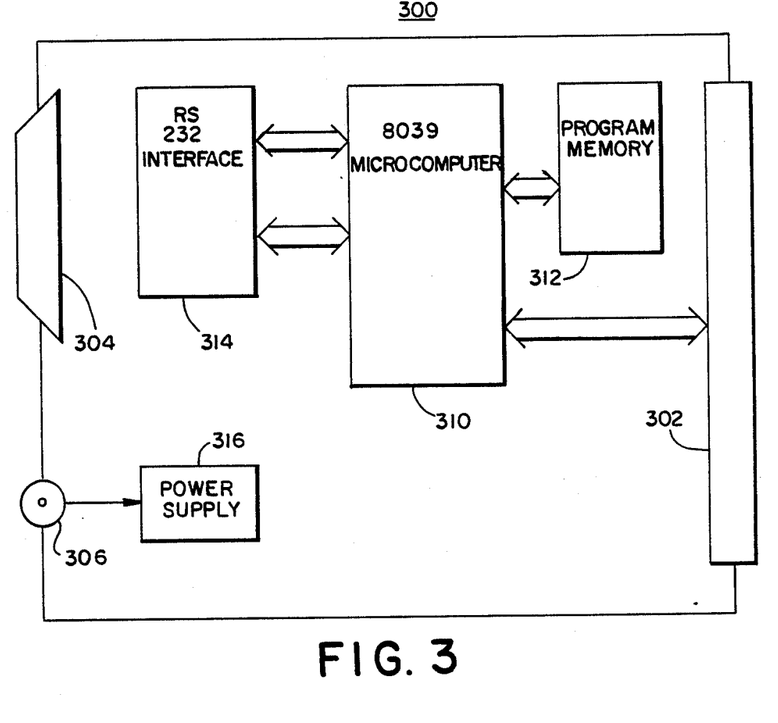
FIG. 3 is a block diagram of the adapter of the present invention for use with the RAM package of FIGS. 1A and 1B.

FIG. 3 is a block diagram of the adapter circuitry of the present invention designated generally 300. It comprises a connector 302 for coupling to the edge connector 36 of the RAM package 10, an RS-232 interface connector 304 and a connector 306 for coupling to an external AC-DC convertor to furnish power. Internally the adapter circuit 300 comprises an Intel 8039 microcomputer 310 with a separate programmable memory chip 312, RS-232 interface circuitry 314, and a power supply 316 from which all operating voltages are derived. The power supply is coupled to connector 306 to receive 9 volts from the external AC-DC converter.

Through connector 302, the adapter 300 accepts the RAM package 10 simply as another device within the addressable range. As such, the adapter 300 has complete control over the RAM package 10 and can read or write any RAM package memory location as well as read or set the RAM package real-time clock 14.

Through connector 304, the adapter 300 sends and receives messages consisting of plain-text, ASCII characters in RS-232 format with which many common devices (terminals, personal computers, modems, etc.) are compatible. Incoming messages are interpreted as commands to perform various servicing functions on the RAM package. Outgoing messages are sent in response to the received commands.

The repertoire of commands and responses for use via the RS-232 interface is small, but complete. There are commands for dumping RAM package data, writing RAM package data and reading and setting the RAM package real-time clock. Thus, a RAM package may be serviced completely with nothing more than the availability of a common RS-232 interface.

Although RAM package servicing is intended to be performed automatically under computer control, the servicing may be performed manually from a terminal by, for example, an engineer who wishes to troubleshoot a RAM package remotely via the telephone network.

Figure 5:
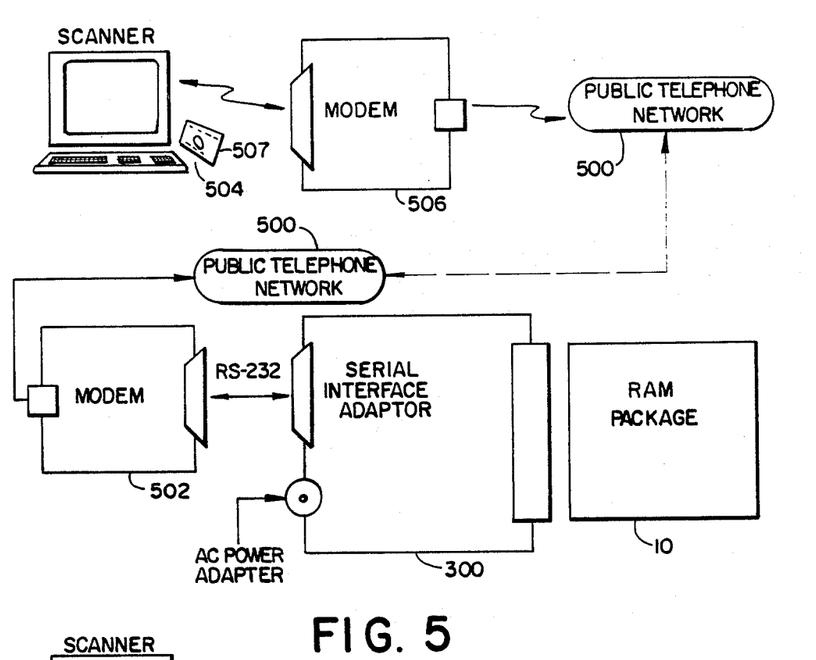
FIG. 5 is a block diagram showing a use of the adapter of FIGS. 3, 4A and 4B in a first operating environment.

FIG. 5 is a block diagram for a complete RAM package remote servicing setup using the public telephone network 500. In this configuration, the adaptor 300 is connected to an off-the-shelf modem 502, such as a Hayes modem, and to the RAM package 10. At the distant station a scanning service computer 504 is connected to another modem 506. An operator originates the service call at the RAM package station by manually dialing the telephone number for the scanning service. After all voice information has been passed to the scanning service by the operator to another human operator, automatic RAM package servicing begins by inserting the RAM package 10 into the adapter 300 at the RAM package end and, at the scanner end, by operator input to the scanning program 507. The scanner controller 504 sends whatever commands it must to service the RAM package 10 while the adapter 300 receives and executes these commands.

Figure 6:
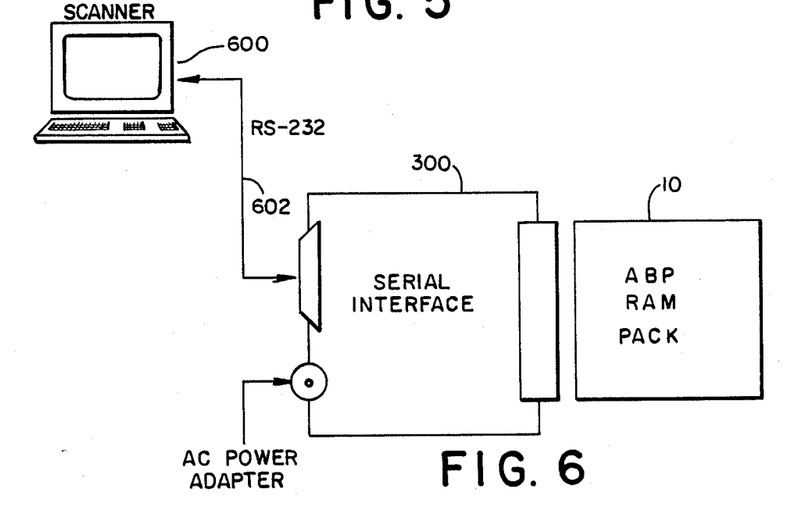
FIG. 6 is a block diagram showing a use of the adapter of FIGS. 3, 4A and 4B in a second operating environment.

The direct connect setup shown in FIG. 6 is an alternative to the telephone network setup of FIG. 5. Communication between the adaptor 300 and the scanner controller 600 is through a direct RS-232 connection 602. This setup is only implemented when the scanner controller 600 and the adapter 300 are within close proximity (i.e. the same room or building). Since the adaptor 300 is insensitive to the type of device which is on the far end of its RS-232 interface, it behaves exactly as for the modem setup of FIG. 5.

Figure 4A:
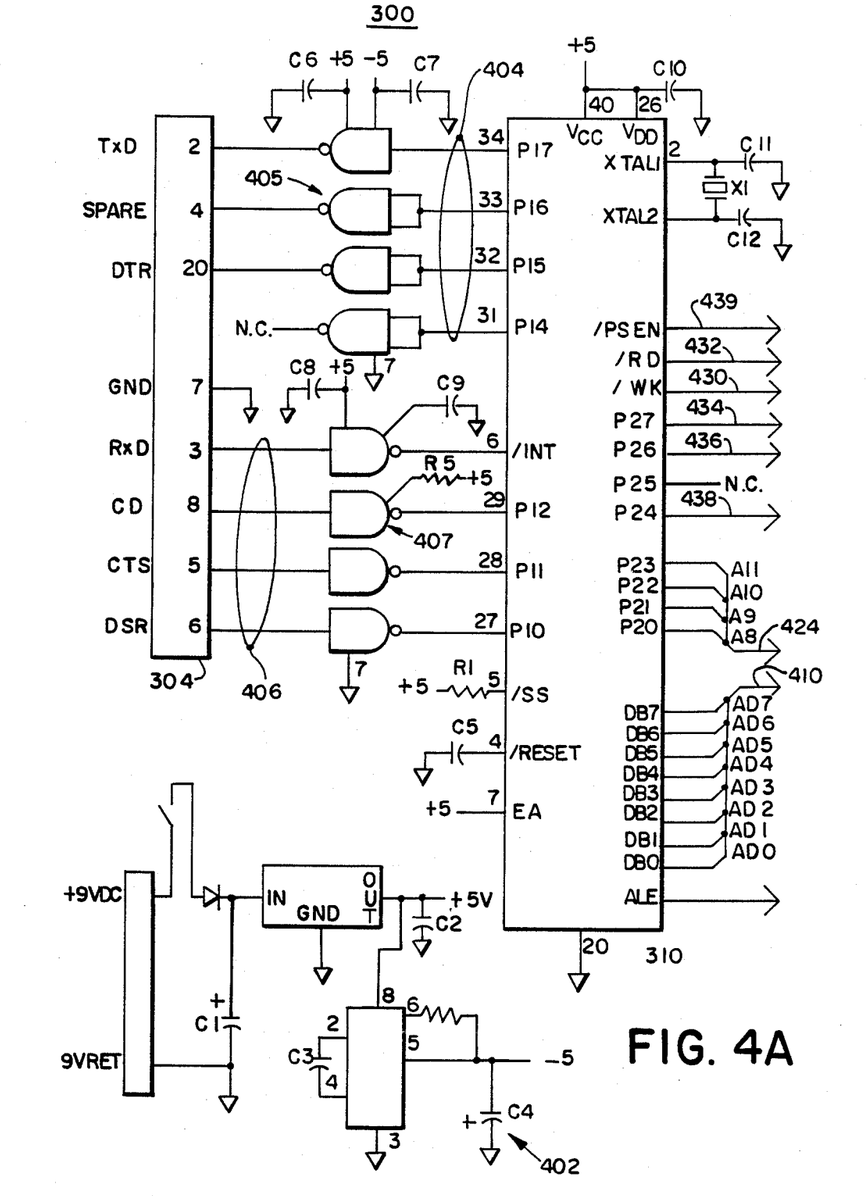
FIGS. 4A and 4B are a more detailed schematic diagram of the block diagram of FIG. 3.
Figure 4B:
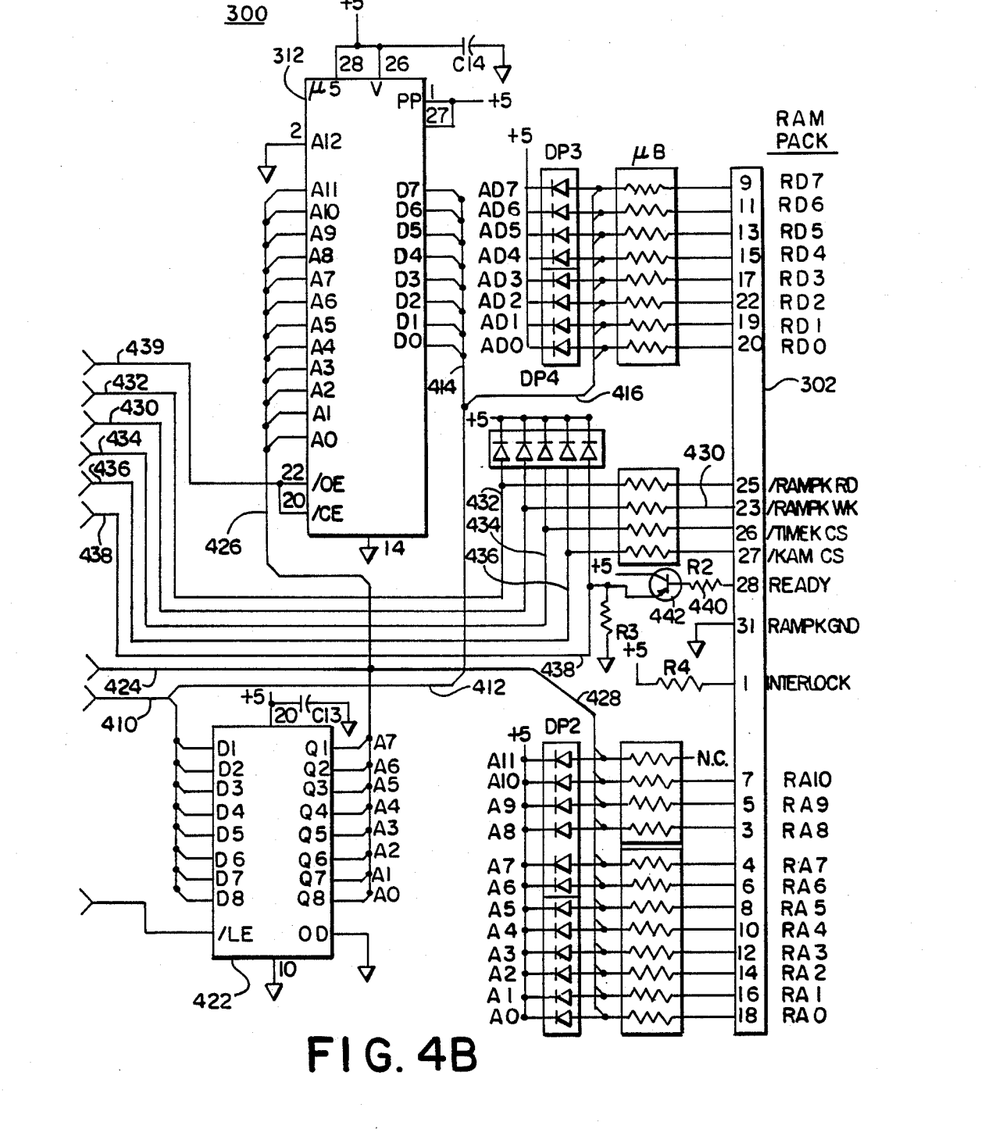

Referring now to FIG. 4, a more detailed schematic of the block diagram of the adapter 300 of FIG. 3 is provided. The adapter 300 is powered by an off the shelf 110 VAC to +9 VDC converter referred to earlier and not shown in the drawings. It is capable of supplying a minimum of 250 MA. It is connected to connector 306 on the adapter 300. The power supply circuit 402 on the adapter 300, also coupled to the connector 306 derives the adapter's operating voltages of +5 VDC and plus or minus 9 VDC from the converter.

The adapter further comprises the RS-232 interface connector 304 which is compatible with the RS-232 serial interface standard. Microcomputer 310 (an Intel 8039) is coupled to connector 304 via a three lead output bus 404 through a Motorola Model No. 1488 line conditioner 405 and via a four lead input bus 406 through a Motorola Model No. 1489 line conditioner 407.

The eight data lines 410 of the microcomputer 310 are coupled via common data bus 412 and data bus 414 to the programmable memory chip 312 and via common data bus 412 and data bus 416 to the RAM package interface connector 302 which couples to the data bus 28 of the RAM package 10. In the preferred embodiment chip 312 is an Intel 2764 device.

The eight data lines 410 also pass through the octal data latch 422 (a Motorola 74LS373 device) where they combine with four microcomputer lines on bus 424 and are coupled to the programmable memory chip 312 by address bus 426 and by address bus 428 to RAM package interface connector 302.

Interface connector 302 is a 34 pin connector adapted for mating engagement with connector 36 of FIG. 2. In the preferred embodiment pin 23 and pins 25-28 are coupled via lines even numbers 430 through 438, respectively, to microcomputer 310. When the appropriate commands are received by the adapter 300 through the RS-232 interface, the program stored in programmable memory chip 312 and executed in the microcomputer 310 cause the microcomputer 310 to transmit a RAM package read signal on line 432; a RAM package write signal on line 430; a timer chip select signal on line 434; or a RAM chip select signal on line 436. The READY signal (described earlier in connection with the RAM package) is provided to the adapter 300 from the RAM package 10 via resistor 440 and transistor 442 on line 438. The microcomputer 310 also provides output and chip enable signals to memory 312 via line 439.

When the adapter is coupled to a modem, it sets the RS-232 DTR terminal (data terminal ready) of connector 304 high to enable the modem. The modem sets the RS-232 CTS terminal (clear to send) high whenever it is able to receive characters. Additionally, the modem sets the CD terminal (carrier detect) high when it detects a carrier from the remote modem. In addition to the above the TD terminal (transmitted data), the RD terminal (received data) and the GND terminal (ground) are implemented when the adapter is coupled to a modem.

The same signals as listed above are implemented when the adapter is coupled to a PC. The adapter sets DTR high to signal that it is on-line and ready to communicate. The PC sets CTS and DTR high whenever it is on-line.

The adapter is reactive since it merely responds to communication initiated by a remote controller without initiating any communication of its own (with the exception of modem initialization commands). Also, the adapter never "times out" while waiting to receive messages and never "gives up" after detecting multiple consecutive communication errors. The controlling terminal (PC) is responsible for communication error-handling.

Communication to and from the adapter comprises blocks of characters organized as whole messages. Data is sent at 1200 bits per second. The character format contains one start bit, seven data bits and two stop bits with no parity bits. All characters are interpreted as 7-bit ASCII. Alphabetic characters may be sent in either upper or lower case, since no distinction between cases is made. Single character ACK or NACK responses to messages are required in some cases as described below in conjunction with the description of each message.

Messages to the adapter 300 have the following general format:

∧A C DDD ... D CCCC where
∧A is the start of message character (ASCII "SOH")
C is one of the allowable commands
DDD ... D is the message content which varies according to the type of message as indicated by "C"
CCCC is the 16-bit (Cyclic Redundacy Code) in 4-character ASCII hex digit format (not used in all comamands)

Messages from the adapter 300 have the following general format:

∧A DDD ... D CCCC where
∧A is the start of message character (ASCII "SOH")
DDD ... D is the message content which varies according to the command which invoked this response
CCCC is the 16-bit CRC in 4-character ASCII hex digit format (used in all cases)

The "SOH" character always starts a new message regardless of any previous communication. Thus, if communication should become confused, the controller can always send an "SOH" to begin a new command. Also, should the controller not care to ACK when appropriate, it can always begin the next command by sending an "SOH".

The CRC, when used, is the 4-digit ASCII hex remainder calculated on all characters following the command character when from the controller and following the ∧A when from the adapter. The calculation is performed on the ASCII characters themselves and not, for example, on the binary conversion of an ASCII digit.

Communication with the adapter 300 is half-duplex. The adapter is not capable of sending and receiving simultaneously. Strict adherence to the listen-talk protocol is required, since the control signals out of the adapter do not indicate when the adapter is not ready to receive serial data. (When the adapter is sending data, for example, it does not recognize incoming data even though its DTR output will be on. This characteristic is due to the requirement of the modem that its DTR input always be enabled.)

In the preferred embodiment there are five commands to which the adapter responds. They are:
I: send identification
U: unlock
D: dump data W: write data T: send/set time Details of each command follow:

The Send identification command, I, to the adapter 300 has the format;

∧AI<CR>

After the adapter 300 receives this message, it responds by sending its ID as follows:

∧AIIIIIIICCCC where IIIIIII is the adapter's 7-character ID and CCCC is the CRC. The ID is compared by the scanner controller with the ID the scanner controller has stored for the adapter. In response to the comparison, the scanner controller sends an ACK or NACK to the adapter. If the adapter receives any character other than an ACK or an SOH, it retransmits its ID as just described.

The Unlock command, U, to the adapter 300 has the format:

∧AUKKKKKCCCC

Details of the Unlock command will be provided later.

In order to obtain data from the RAM package 10, the scanner controller will send a Dump data command, D. This command has the following format:

∧ADFFFLLLCCCC

If CCCC is a correct CRC for this message, the adapter will send the contents of the RAM package from address FFF (first) to address LLL (last). The data message will be of the form     ∧ADDDDDD ... DDCCCC where A is the start of message character, each DD is an ASCII hex byte from the RAM package and CCCC is the CRC. The number of bytes to send cannot be more than 255. Data dumps of 64 or fewer bytes are recommended to minimize the chance of communication errors.

The adapter 300 then expects to receive an ACK or NACK after the data has been sent. If it receives any character other than an ACK or an SOH, it retransmits the data as above. If the CCCC of the command message is incorrect, the adapter 300 will send a NACK. The adapter 300 must be "unlocked" any time before execution of this command. A "locked" adapter will not respond at all to this command.

When writing data to the RAM package 10 through the adapter 300, the scanner controller uses the command write data, W, which has the following format:

∧AWFFFLLLDDDDDD ... DDCCCC

If the CCCC is correct, the adapter 300 will send an ACK and will write each data byte DD starting with the first to the RAM package starting at address FFF and ending at LLL. No more than 64 bytes will be accepted in this message. Otherwise, the adapter 300 will send a NACK. The adapter must be "unlocked" any time before execution of this command. A "locked" adapter will not respond at all to this command.

When the controller wishes to check the time of the real time clock 14 in the RAM package 10, it sends a Send time command, T. It has the format     ∧AT<CR>

The adapter responds to this message by sending the time from the RAM package real-time clock as follows:

∧AMMDDHHMMSSCCCC where the first MM is the numeric month, DD is the day, HH is the hour, the second MM is the minute, SS is the second and CCCC is the CRC. The adapter then expects to receive an ACK or a NACK. If it receives any character other than an ACK or an SOH, it retransmits an updated clock reading in the above format. The adapter 300 must be "unlocked" any time before execution of this command. A "locked" adapter will not respond at all to this command.

It is sometimes desirable or necessary to change or set the clock time in the RAM package 10, particularly after the batteries on the RAM package are replaced. To accomplish this a Set time command, also T, is used. It has the following format:

∧ATMMDDHHMMCCCC

If CCCC is correct, the adapter 300 sends an ACK, and reprograms the RAM package real time clock 14. Otherwise, it will send a NACK. The adapter 300 must be "unlocked" any time before execution of this command. A "locked" adapter will not respond at all to this command.

As described above, the adapter 300 must be unlocked with a key message (U) before it will respond to any RAM package servicing commands. Whenever the adapter detects an interruption of communication or the absence of a RAM package (no READY signal), it locks up and must be unlocked again before it will resume RAM package service.

"Unlocking" is accomplished as follows:

The controller sends the "send ID" command to determine the individual identity of the adapter which is on-line. The adapter 300 responds by sending its ID.

The controller looks up in its data base either the individual key or the master key which corresponds to that ID and sends it in the "unlock" message to the interface. Remember the U command format is:

∧AUKKKKKCCCC, where KKKKK is the key number.

Upon receipt of this message, the adapter 300 compares the key "KKKKK" to its individual key as well as to its master key. If KKKKK matches either the individual key or its master key and if CCCC is a correct CRC for the message, the adapter 300 will send an ACK, unlock and allow data communication. Otherwise, it will send a NACK, lock up and not adknowledge RAM package servicing commands.

The individual key number is a number used by the owner or user of the adapter and RAM package and by a commercial scanner controller. The master key number is a number used by the "adapter" manufacturer in order to service, maintain and update adapter programs. The ID and the individual and master key numbers are programmed into the EPROM 312 at assembly time.

When the Dump data command, D, is received, the microcomputer 310 reads each requested byte by setting the RAM package read line 432 low and then the RAM chip select line 436 low. Then the recorded blood pressure data in the RAM 12 is transmitted to the remote scanner con-troller. For a Write data command, W, the micro-computer 310 writes each requested byte by setting the RAM write line 430 low and then the RAM chip select line 436 low. Typically, data written to RAM 12 from the controller involves operational data relating to how often blood pressure is to be taken, etc.

When a T (set time) command is received, the microcomputer 310 sets the RAM package 10 write line 430 low and the Timer chip select line 434 low. The line 430 is coupled through OR gate 60 in FIG. 1B to both the write lines for the RAM 12 and timer 14.

RAM package 10 provides a READY signal on line 438 from NAND gate 58 in FIG. 1B when the RAM package is properly connected to an external device. The adapter 300 uses this READY signal to respond to the ID and unlock command sequences. If the READY signal is not present, the adapter will remain locked. The adapter 300 provides the necessary high signal on pin 1 of the edge connector in FIG. 2 to activate the READY signal.

What is claimed is:

1. An apparatus for interfacing a portable medical monitor with a remote scanner controller comprising:
   a removable RAM package selectively couplable to the medical monitor, said removable RAM package comprising:
   a power supply;
   a RAM connected to a parallel multibit data bus and a parallel multibit address bus, said data bus and said address bus being connected to a first multipin connector, said first multipin connector for selectively connecting the removable RAM package to the medical monitor such that the medical monitor can store data in said RAM, said RAM being powered by said power supply; and
   a real time timer circuit connected on said data bus and on said address bus, said timer circuit being powered by said power supply;
   said interfacing apparatus further comprising:
   means for adapting said RAM package to be serviced by the remote scanner controller through a standard serial interface, said adapting means including a serial interface connector for selectively coupling said adapting means to the scanner controller, said adapting means also including a second multipin connector adapted for mating engagement with said first multipin connector of said RAM package such that said RAM package can be selectively coupled to said adapting means, said adapting means being responsive to engagement of said first and second multipin connectors and command signals received from the remote scanner controller for enabling the scanner controller to service said RAM package.

2. The apparatus of claim 1 wherein said adapting means further comprises:
   a microcomputer chip coupled to said serial interface connector and said second multipin connector, said microcomputer chip being adapted to interrogate the scanner controller by transmitting an identification command thereto, said microcomputer chip being responsive to a key number code received from the scanner controller in response to the interrogation for enabling the scanner controller to service said RAM package.

3. The apparatus of claim 2 wherein said adapting means further comprises:
   a programmable memory chip coupled to said microcomputer chip for storing operating commands for said microcomputer chip, said programmable memory chip being programmed with a unique key number code, said microcomputer chip being adapted to compare the key number code received from the scanner controller with that stored in said programmable memory chip and to enable the scanner controller to service said RAM package if the two key number codes are the same.

4. The system of claim 1 wherein said serial interface comprises a standard RS-232 interface.

5. A system for servicing a portable medical monitor comprising:
   a removable RAM package selectively connectable to the medical monitor, said RAM package comprising:
   a power supply;
   a RAM connected to a parallel multibit data bus and a parallel multibit address bus, said data bus and said address bus being connected to a first multipin connector, said first multipin connector for selectively connecting the removable RAM package to the medical monitor such that the medical monitor can store data in said RAM package, said RAM being powered by said power supply; and
   a real time timer circuit connected on said data bus and on said address bus, said timer circuit being powered by said power supply;
   said system further comprising a scanner controller for servicing said RAM package through a standard serial interface; and
   means connectable between said scanner controller and said RAM package for adapting said RAM package to be serviced by said scanner controller through a standard serial interface, said adapting means including a serial interface connector for selectively connecting said adapting means to the standard serial interface, said adapting means also including a second multipin connector adapted for mating engagement with said first multipin connector of said RAM such that said RAM can be selectively coupled to said adapting means, said adapting means including means for controlling access to said RAM package through said serial interface.

6. A system for servicing a portable medical monitor comprising:
   a removable RAM package selectively connectable to the medical monitor, said RAM package comprising:
   a power supply;
   a RAM connected to a parallel multibit data bus and a parallel multibit address bus, said data bus and said address bus being connected to a first multipin connector, said first multipin connector for selectively connecting the removable RAM package to the medical monitor such that the medical monitor can store data in said RAM package, said RAM being powered by said power supply; and
   a real time timer circuit connected on said data bus and on said address bus, said timer circuit being powered by said power supply;

said system further comprising a scanner controller for servicing said RAM package through a standard serial interface; and means connectable between said scanner controller and said RAM package for adapting said RAM package to be serviced by said scanner controller through a standard serial interface, said adapting means including a serial interface connector for selectively connecting said adapting means to the standard serial interface, said adapting means also including a second multipin connector adapted for mating engagement with said first multipin connector of said RAM such that said RAM can be selectively coupled to said adapting means, said adapting means including means for controlling access to said RAM package through said serial interface.

7. The system of claim 5 wherein said adapting means further comprises:

means in response to at least one of said controller commands for reading data including blood pressure data stored in said RAM through said serial interface; and means in response to at least one of said controller commands for writing control data to said RAM through said serial interface to control the acquisition and storage of said blood pressure data when said RAM package is coupled to said portable medical monitor.

8. The system of claim 6 wherein said access control means further comprises:

means for storing a key number for identifying said adapting means;

means for receiving a key number from said scanner controller;

means responsive to said receiving means for comparing the key number received from said scanner controller with the key number stored in said storing means and unlocking said serial interface if the two compared key numbers are the same whereby said RAM package can be serviced by said scanner controller.

9. The system of claim 6 wherein said access control means further comprises:

means for preventing unlocking of said serial interface if said first multipin connector of said RAM package is not coupled to said second multipin connector of said adapting means.

10. The system of claim 9 wherein said removable RAM package further comprises:

an interlock circuit for providing a READY signal to said prevention means when said interlock circuit senses a predetermined voltage level on a predetermined pin location of said second multipin connector of said adapting means when said first and second connectors are matingly engaged whereby said prevention means is disabled.

11. The system of claim 5 wherein said adapting means and said scanner controller are coupled to respective first and second modems, respectively, such that said first modem of said adapting means can be coupled to said second modem of said scanner controller by the telephone network.

12. A method for interfacing a portable medical monitor with a remote scanner controller comprising the steps of:

(a) coupling a removable RAM package to the medical monitor such that the medical monitor can store monitored data in the memory of the removable RAM package;

(b) coupling the removable RAM package to a communication adapter and coupling the communication adapter to the remote scanner controller such that the removable RAM package can be placed in data communication with the remote scanner controller;

(c) interrogating the remote scanner controller to insure data is not transmitted to a scanner controller which is not authorized to receive the data;

(d) enabling transmission of data to the remote scanner controller if, after interrogation, the remote scanner controller is determined to be authorized to receive the data; and (e) transmitting data stored in the RAM package to the authorized scanner controller in response to commands received from the scanner controller.

13. The method as recited in claim 12 wherein the step of interrogating the remote scanner controller comprises the substeps of:

(f) sending an indentification command to the remote scanner controller wherein the identification command identifies the interface adapter which originated the command;

(g) responding to the identification command received from the interface adapter to send a corresponding key number to the interface adapter; and (h) responding to the key number received from the scanner controller to compare the received key number with a key number stored in a memory location of the interface adapter and determining that the scanner controller which originated the received key number is authorized if the received key number matches the stored number and, determining that the scanner controller which originated the received key number is unauthorized if the received key number does not match the stored key number.

14. The method as recited in claim 12 further comprising the step of converting parallel data received from the RAM package to standard serial data compatible with standard serial connectors and transmitting serial data to the scanner controller.

15. The method as recited in claim 12 further comprising the step of monitoring the first connection between the interface connector and the RAM package and monitoring the second connection between the interface adapter and the remote scanner controller to determine if either the first or second connection is interrupted at any time following the decision that the remote scanner controller is authorized to receive data and, if so, discontinuing transfer of data from the RAM package to the remote scanner controller until the scanner controller is again determined to be authorized.

* * * * *

UNITED STATES PATENT AND TRADEMARK OFFICE
CERTIFICATE OF CORRECTION

PATENT NO. : 4,754,401

DATED : June 28, 1988

INVENTOR(S) : Francis X. Kaczynski

It is certified that error appears in the above-identified patent and that said Letters Patent is hereby corrected as shown below:

Delete claims 6 and 7, and insert as follows:

6. The system of claim 5 wherein said adapting means further comprises:

>means in response to at least one of said controller commands for reading data including blood pressure data stored in said RAM through said serial interface; and >means in response to at least one of said controller commands for writing control data to said RAM through said serial interface to control the acquisition and storage of said blood pressure data when said RAM package is coupled to said portable medical monitor.

7. The system of claim 6 wherein said adapting means further comprises:

>means in response to said controller commands for setting the timing parameters in said real time timer through said serial interface; and >means in response to at least one of said controller commands for reading the timing parameters in said real time timer through said serial interface.

Signed and Sealed this

Fourteenth Day of February, 1989

*Attest:*

DONALD J. QUIGG

*Attesting Officer*     *Commissioner of Patents and Trademarks*